United States Patent [19]

Ikushima et al.

[11] 4,164,569
[45] Aug. 14, 1979

[54] STABILIZED SOFT GELATIN CAPSULE COMPOSITION OF 1 α-HYDROXY-VITAMIN D

[75] Inventors: Heizi Ikushima, Kawaguchi; Hiroto Nakano, Kodaira; Kazuo Igusa, Tokorozawa; Sadao Bessho, Tokyo, all of Japan

[73] Assignee: Chugau Seiyaku Kabushiki Kaisha, Tokyo, Japan

[21] Appl. No.: 786,483

[22] Filed: Apr. 8, 1977

[30] Foreign Application Priority Data

Apr. 19, 1976 [JP] Japan .................................. 51-43615

[51] Int. Cl.$^2$ ..................... A61K 31/00; A61K 31/59; A61K 31/195
[52] U.S. Cl. .................................. 424/174; 424/236; 424/319
[58] Field of Search ..................... 424/174, 236, 319

[56] References Cited

U.S. PATENT DOCUMENTS

| | | | |
|---|---|---|---|
| 2,432,698 | 12/1947 | Taub et al. | 424/236 |
| 2,862,852 | 12/1958 | Cannalonga | 424/236 |
| 3,138,532 | 6/1964 | Aiello et al. | 424/236 |
| 3,833,622 | 9/1974 | Babcock et al. | 424/236 |
| 3,864,469 | 2/1975 | Reiser et al. | 424/236 |
| 3,869,539 | 3/1975 | Kring et al. | 424/236 |
| 3,887,545 | 6/1975 | Iacobelli et al. | 260/239.55 R |
| 3,907,843 | 9/1975 | DeLuca et al. | 260/397.2 |
| 3,943,238 | 3/1976 | Kobayashi et al. | 424/37 |

FOREIGN PATENT DOCUMENTS 2019839 11/1970 Fed. Rep. of Germany .

OTHER PUBLICATIONS

The Merck Index, 9th Ed., No. 8495 (p. 1126) (1976).
Kirk–Othmer, Encyclopedia of Chem. Tech. 18, pp. 589–597.
Chem. Abstract, 75, 52752 (q) (1971).
Science 180, pp. 190–191 (1973), Holick, et al.
The Pharmacological Basis of Therapeutics, pp. 1687–1695 (1966).

*Primary Examiner*—Douglas W. Robinson
*Attorney, Agent, or Firm*—Browdy and Neimark

[57] ABSTRACT

A soft gelatin capsule preparation of a 1α-hydroxy-vitamin D which contains sorbic acid or its salt and a process for preparing the preparation are disclosed. Sorbic acid or its salt which is incorporated in a soft gelatin capsule and/or an oily diluent acts as a preservative for gelatin and as a stabilizer for the vitamin D.

11 Claims, No Drawings

4,164,569

STABILIZED SOFT GELATIN CAPSULE COMPOSITION OF 1 α-HYDROXY-VITAMIN D

FIELD OF THE INVENTION

This invention relates to a stabilized preparation of a 1α-hydroxy-vitamin D encapsulated in a soft gelatin capsule and a process for preparing the same.

BACKGROUND OF THE INVENTION

In recent years, a vitamin D having a hydroxy group at 1 α position, for example, 1α-hydroxy-vitamin $D_3$ or 1α,25-dihydroxy-vitamin $D_3$ has been given attention due to its strong vitamin D activities.

However, since vitamin D is usually used in a very small dose per single administration, it is difficult to give a predetermined exact amount per unit dose in case the vitamin D is formulated in the form of pill or tablet. Further, vitamin D is very sensitive to exposure to light, particularly to ultraviolet light and, therefore, its handling or treatment should be effected under light-intercepted conditions and also a pharmaceutical preparation containing the vitamin D should be stored without exposure to light.

From the viewpoint of stability of the vitamin D, the most desirable process for manufacturing a pharmaceutical preparation is to dissolve 1α-hydroxy-vitamin D in an oily diluent and then encapsulate the solution with a soft capsule.

The encapsulation in a soft gelatin capsule is advantageous because the press-through-pack can be employed with the use of transparent plastic film capable of intercepting ultraviolet light to reduce the deactivation of the vitamin D due to the exposure to ultraviolet light.

However, the inventors of this invention experimentally found that, even in case 1α-hydroxy-vitamin D was dissolved in an oily diluent and encapsulated in a soft gelatin capsule and the capsule preparation was subjected to the press-through-pack to intercept ultraviolet light, a considerable amount of 1α-hydroxy-vitamin D contained in the preparation lost its vitamin D activities.

The inventors continued their study on such deactivation phenomenon to find that the phenomenon is induced due to the effect of a p-hydroxybenzoic ester which is conventionally incorporated into a soft gelatin capsule as a preservative for gelatin. On the other hand, since gelatin, the base material for a capsule is putrescible and especially, such putrefaction is accelerated in case a soft gelatin capsule contains a softening agent, such as glycerin, polyethylene glycol, propylene glycol or the like, for preventing the capsule from hardening, a preservative should be present in the capsule.

The inventors focused their study on the preservative for gelatin and found that sorbic acid or its salt which is a suitable preservative does not induce the deactivation of a 1α-hydroxy-vitamin D and, besides, heightens its stability. Based on these facts, they finally completed the present invention.

SUMMARY OF THE INVENTION

According to the present invention, a capsule preparation containing a 1α-hydroxy-vitamin D in a stabilized state and a process for preparing such capsule preparation can be provided. The preparation comprises a soft gelatin capsule filled with a solution of a 1α-hydroxy-vitamin D in an oily diluent.

DESCRIPTION OF THE PREFERRED EMBODIMENTS

A 1α-hydroxy-vitamin D which may be applied to the present invention includes a vitamin D having a hydroxyl group at 1α position, for example, 1α-hydroxy-vitamin $D_3$, 1α,25-dihydroxy-vitamin $D_3$, 1α,24-dihydroxy-vitamin $D_3$ or the like.

For an oily diluent, any oil which is liquid around room temperature and does not decompose a 1α-hydroxy-vitamin D may be used in the present invention, but a triglyceride of fatty acid, an unsaturated middle chain fatty acid such as linoleic acid, cotton seed oil, olive oil, corn oil and the like are preferable.

Sorbic acid may be used as it is or as a pharmaceutically acceptable salt, but sorbic acid, or sodium or potassium sorbate is preferable. It will be understood that a mixture of sorbic acid with one or more salts in any suitable proportion may be used in the present invention. Sorbic acid, its salt or a mixture thereof is preferably present in a soft gelatin capsule in an amount of from 0.2 to 1% by weight based on the total weight of the capsule or preferably present in an amount of from 0.005 to 1% by weight based on the diluent.

The thus formulated and encapsulated vitamin D is recognized to be highly stable.

The present invention is further illustrated by the following Experiments and Examples, but they are not to be construed as limiting the scope of this invention.

Experiment 1

For comparison, various capsule preparations containing 1α-hydroxy-vitamin $D_3$ were prepared as disclosed in the Example 1 hereinbelow except for the use of a capsule containing a different preservative or containing no preservative. These capsule preparations and the capsule preparation prepared in Example 1 were covered by a transparent film capable of intercepting ultraviolet light and exposed to sunbeams for 2 weeks. After the exposure, the amount of active 1α-hydroxy-vitamin $D_3$ in each of the capsule preparations was determined by the use of high speed liquid chromatography.

The test results are shown in Table 1 below. Incidentally, the value shown in Table 1 is the amount of 1α-hydroxy-vitamin $D_3$ as calculated by assuming the amount of 1α-hydroxy-vitamin $D_3$ in the preservative free capsule to be 100.

Table 1

| Preservative | Value |
| --- | --- |
| not used | 100 |
| methyl p-hydroxybenzoate | 64 |
| ethyl p-hydroxybenzoate | 67 |
| propyl p-hydroxybenzoate | 70 |
| butyl p-hydroxybenzoate | 70 |
| isopropyl p-hydroxybenzoate | 69 |
| isobutyl p-hydroxybenzoate | 71 |
| sodium tetrahydroxyacetate | 85 |
| sodium benzoate | 87 |
| sorbic acid | 115 |
| potassium sorbate | 124 |
| sodium sorbate | 122 |

Experiment 2

By the method similar to that described in Experiment 1, the effect of sorbic acid or its salt for reducing the deactivation of some vitamin $D_3$ was determined by the use of the capsule preparation prepared in Example 2 hereinbelow.

The test results are shown in Table 2 below. In Table 2, the value is the amount of each vitamin $D_3$ as calculated by assuming the amount of each vitamin $D_3$ dissolved in the diluent free from sorbic acid or its salt.

Table 2

| Test Compound | Concentration | $1\alpha$-hydroxy-vitamin $D_3$ | $1\alpha,25$-dihydroxy-vitamin $D_3$ | $1\alpha,24$-dihydroxy-vitamin $D_3$ |
|---|---|---|---|---|
| not used | — | 100 | 100 | 100 |
| sorbic acid | 0.05% | 128 | 131 | 120 |
|  | 0.50% | 126 | 136 | 123 |
| potassium sorbate | 0.005% | 108 | — | — |
|  | 0.02% | 124 | — | — |
| sodium sorbate | 0.01% | — | 110 | — |
|  | 0.05% | — | 115 | — |

Example 1

In a triglyceride of middle-chain fatty acid (O.D.O.: manufactured by Nisshin Seiyu Kabushiki Kaisha) was dissolved $1\alpha$-hydroxy-vitamin $D_3$ at a concentration of 10 μg/ml. Separately, the ingredients specified below were blended while warming to form a fusion.

| Ingredients | Proportion (parts by weight) |
|---|---|
| Gelatin | 10 |
| Glycerin | 5 |
| Preservative | 0.08 |
| Purified water | 14 |

The fusion was formed to soft gelatin capsule which was filled with the solution of $1\alpha$-hydroxy-vitamin $D_3$ in an amount of 1 μg per each capsule in a conventional manner by the use of an encapsulating machine.

Example 2

In the triglyceride of middle chain fatty acid (O.D.O.) was dissolved sorbic acid or its salt in a predetermined amount and then to the resulting solution was dissolved a $1\alpha$-hydroxy-vitamin $D_3$ at a concentration of 10 μg/ml. In the same manner as described in Example 1, the above solution was charged in the soft gelatin capsule to form a soft gelatin capsule preparation. The used capsule was the same as that of Example 1 except for containing no preservative therein.

What is claimed is:

1. A method for stabilizing $1\alpha$-hydroxy-vitamin D, encapsuled in a soft gelatin capsule, against deactivation caused by ultraviolet light, comprising:
    incorporating an ultraviolet light deactivation preventive amount of sorbic acid, its salt or a combination thereof in the gelatin of said capsule or with the vitamin D encapsulated by said capsule.

2. A method according to claim 1 wherein said salt of sorbic acid is selected from the group consisting of sodium sorbate and potassium sorbate.

3. A method according to claim 1 wherein said $1\alpha$-hydroxy-vitamin D is selected from the group consisting of $1\alpha$-hydroxy-vitamin $D_3$, $1\alpha,25$-dihydroxy-vitamin $D_3$ and $1\alpha,24$-dihydroxy-vitamin $D_3$.

4. A method according to claim 1 wherein said $1\alpha$-hydroxy-vitamin D is $1\alpha$-hydroxy-vitamin $D_3$.

5. A method in accordance with claim 1 wherein said soft gelatin capsule comprises a capsule formed from gelatin and a softening agent therefor.

6. A method in accordance with claim 1 wherein incorporating step comprises incorporating said sorbic acid, salt or combination in both the gelatin of said capsule and with the vitamin D encapsulated by said capsule.

7. A method according to claim 6 wherein the amount of said sorbic acid, its salt or combination thereof present in said soft gelatin capsule ranges from 0.2 to 1% by weight based on said capsule.

8. A method in accordance with claim 1 wherein incorporating step comprises incorporating said sorbic acid, salt or combination only in the gelatin of said capsule.

9. A method in accordance with claim 1 wherein incorporating step comprises incorporating said sorbic acid, salt or combination only with the vitamin D encapsulated by said capsule.

10. A method in accordance with claim 9 wherein said incorporating step comprises incorporating said sorbic acid, salt or combination only with the vitamin D composition encapsulated by said capsule and wherein the amount of said sorbic acid, salt or combination present in said composition ranges from 0.005 to 1% by weight based on said diluent.

11. A method in accordance with claim 1 wherein said vitamin D is present within said capsule as part of a composition also including an oily diluent selected from the group consisting of triglyceride of fatty acid, unsaturated middle chain fatty acid, cotton seed oil, olive oil and corn oil.

* * * * *